(12) United States Patent  
Johnston

(10) Patent No.: US 8,576,392 B2
(45) Date of Patent: Nov. 5, 2013

(54) MULTIPLEXED OPTICAL FIBER CRACK SENSOR

(75) Inventor: Robert T. Johnston, Orlando, FL (US)

(73) Assignee: Siemens Energy, Inc., Orlando, FL (US)

( * ) Notice: Subject to any disclaimer, the term of this patent is extended or adjusted under 35 U.S.C. 154(b) by 155 days.

(21) Appl. No.: 13/085,617

(22) Filed: Apr. 13, 2011

(65) Prior Publication Data

US 2012/0198849 A1    Aug. 9, 2012

Related U.S. Application Data

(63) Continuation-in-part of application No. 13/023,785, filed on Feb. 9, 2011.

(51) Int. Cl.
*G01N 21/00*    (2006.01)
*G01B 11/16*    (2006.01)

(52) U.S. Cl.
CPC ............... *G01N 21/00* (2013.01); *G01B 11/16* (2013.01)
USPC ........ 356/237.1; 356/237.2; 356/32; 356/73.1

(58) Field of Classification Search
CPC ..................................................... G01N 21/00
USPC .................... 356/237.1–237.5, 32–35.5, 73.1
See application file for complete search history.

(56) References Cited

U.S. PATENT DOCUMENTS

| 5,553,504 | A | * | 9/1996 | Lyons et al. ................... 73/799 |
| 5,723,857 | A | * | 3/1998 | Underwood et al. ..... 250/227.14 |
| 5,748,312 | A | * | 5/1998 | Kersey et al. ................. 356/478 |
| 5,942,750 | A | * | 8/1999 | Sannerhaugen et al. . 250/227.14 |
| 6,233,373 | B1 | * | 5/2001 | Askins et al. .................... 385/12 |
| 6,256,090 | B1 | * | 7/2001 | Chen et al. .................... 356/73.1 |
| 6,563,969 | B2 | * | 5/2003 | Ames ................................ 385/12 |
| 6,668,105 | B2 | * | 12/2003 | Chen et al. ....................... 385/13 |
| 6,876,786 | B2 | * | 4/2005 | Chliaguine et al. ............. 385/13 |
| 7,333,680 | B2 | * | 2/2008 | Yong et al. ....................... 385/12 |
| 7,495,750 | B2 | * | 2/2009 | Hwang et al. ................... 356/32 |
| 2002/0028034 | A1 | * | 3/2002 | Chen et al. ....................... 385/12 |

(Continued)

FOREIGN PATENT DOCUMENTS

| EP | 1519181 A1 | 3/2005 |
| JP | 2001021384 A | 1/2001 |
| WO | 02052242 A2 | 7/2002 |

OTHER PUBLICATIONS

Fundamentals of FBG Optical Sensing; http://zone.ni.com/devzone/cda/tut/p/id/11821; National Instruments Corporation; Sep. 21, 2010; Tutorial.

*Primary Examiner* — Michael P Stafira

(57) ABSTRACT

An optical fiber crack detector that includes a plurality of FBG sensors positioned within one or more fibers that are operable to reflect a defined wavelength of an optical input beam. The crack detector includes a light source for generating the optical input beam that propagates down the optical fiber and interacts with the FBG sensors. A wavelength of the optical beam that is reflected by the FBG sensors is detected, and if a crack in the component damages the fiber between an FBG sensor and the detector circuit, where one or more of the reflected signals are not received, the detector knows that a crack has occurred. By strategically placing a plurality of the FBG sensors along the fiber, a crack that damages the fiber in multiple locations between multiple FBG sensors, or in multiple fibers, can provide an indication of the length of the crack.

20 Claims, 6 Drawing Sheets

(56) References Cited

U.S. PATENT DOCUMENTS

| | | | |
|---|---|---|---|
| 2003/0021306 A1* | 1/2003 | Fernald et al. | 372/20 |
| 2004/0067002 A1* | 4/2004 | Berg et al. | 385/12 |
| 2005/0146076 A1* | 7/2005 | Alexander et al. | 264/257 |
| 2005/0163414 A1 | 7/2005 | Takeya et al. | |
| 2006/0056959 A1 | 3/2006 | Sabol et al. | |
| 2006/0056960 A1* | 3/2006 | Sabol et al. | 415/118 |
| 2008/0204707 A1* | 8/2008 | Hwang et al. | 356/35.5 |
| 2009/0052832 A1* | 2/2009 | Roberts | 385/13 |
| 2009/0202194 A1* | 8/2009 | Bosselmann et al. | 385/12 |

* cited by examiner

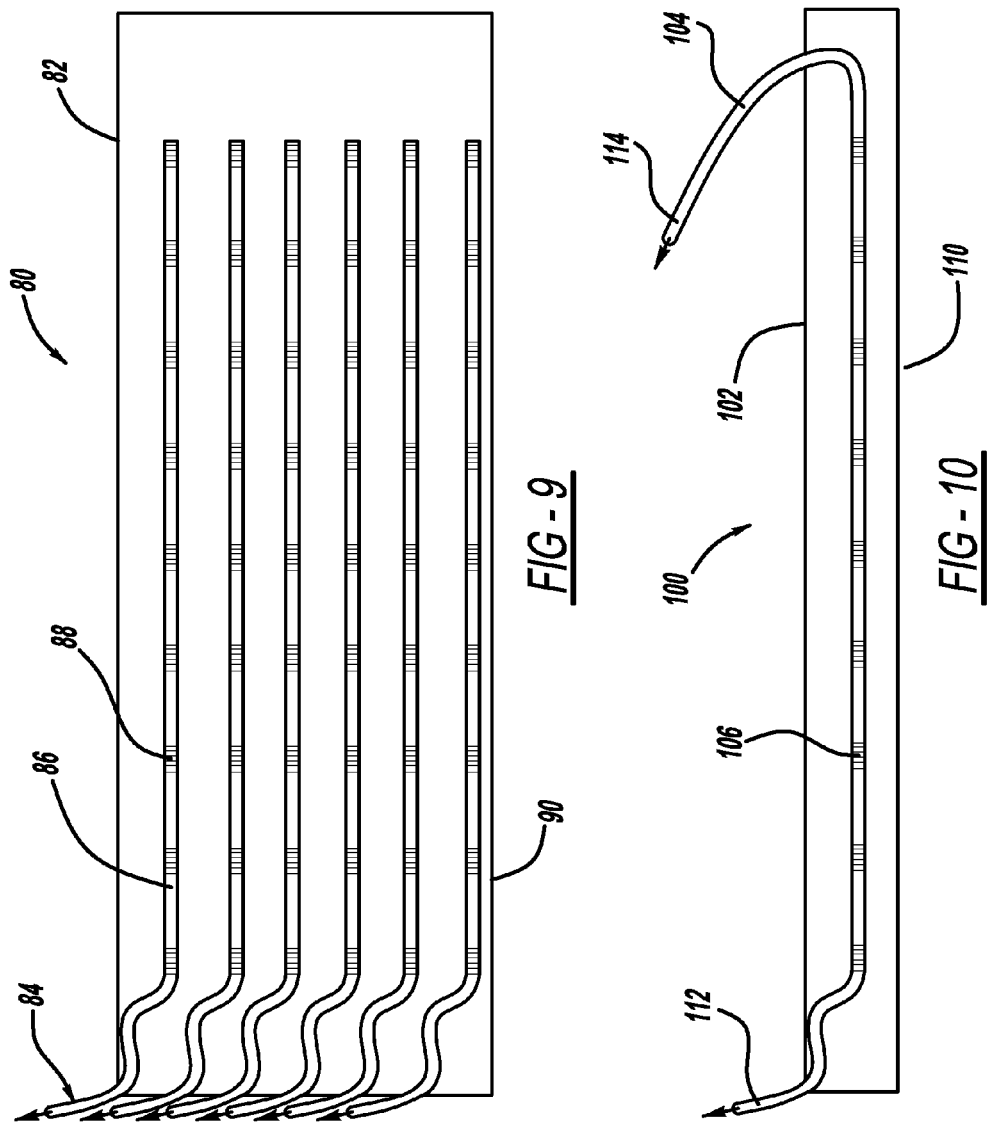

MULTIPLEXED OPTICAL FIBER CRACK SENSOR

CROSS REFERENCE TO RELATED APPLICATIONS

This application is a continuation-in-part application of U.S. patent application Ser. No. 13/023,785, titled, Multiplexed Optical Fiber Wear Sensor, filed Feb. 9, 2011.

BACKGROUND OF THE INVENTION

1. Field of the Invention

This invention relates generally to an optical fiber crack detector and, more particularly, to an optical fiber crack detector that employs fiber Bragg grating (FBG) sensors.

2. Discussion of the Related Art

Many devices, machines and associated systems employ moveable components that may interact with each other in a manner that may cause undesirable wear, defects, cracks, etc. on the components. For example, turbines, compressors and other machines include motors that rotate shafts having blades and other elements disposed thereon. Operation of such machines may cause unwanted contact of the blades and other moving components with housings and other structures within the machine. This unwanted contact could be caused by many factors, such as thermal expansion, high shaft rotation speed, motor surge, etc. Also, some of these types of machines may employ what are known in the art as knife-edge seals that include a thin edge positioned on a rotating member that contacts a stationary structure and provides a pressure seal from one side of the edge to the other. That is, the knife edge seal limits flow and results in a differential pressure. This rotating contact point between the knife-edge and the structure must be small to limit flow, thus causing wear on both components if they inadvertently touch during machine operation, typically due to non-standard operating conditions, such as surge.

Such component wear may be excessive enough where it would affect the performance and operation of the component, system or machine that they are a part of. Various things can be done to reduce the wear, such as providing lubricants, appropriate low friction materials, favorable orientation between components, etc. However, these available remedies are not always adequate, and excessive wear may still occur. Some machines and systems allow component wear to be detected by visual inspection. However, there are many applications where such visual inspection is not possible, or is not feasible because the time, cost, labor, etc. necessary for the inspection is too great.

Many attempts have been made in the art to detect component wear and other defects by providing sensors within the component at the wear location that detect the removal of material and wear on the component. For example, it is known to embed optical fibers into the surface of a component at a location where it is desired to detect wear, and use a light beam propagating down the fiber and suitable detection circuitry to determine if the fiber has been broken as a result of the wear. Other systems that employ optical fibers are also known.

U.S. patent application Ser. No. 12/724,531, filed Mar. 16, 2010, titled Fiber Optic Sensor System for Detecting Surface Wear, assigned to the assignee of this application and herein incorporated by reference, discloses a fiber optic sensor for detecting surface wear. One or more fibers are provided within the component being detected, where one end of the fiber including a re-emission portion is positioned near the wear surface. A light beam propagating down the optical fiber contacts the re-emission portion, creating a return beam that is detectable. The re-emission portion can be a reflective element that reflects the beam or a florescent element that fluoresces in response to the beam. If the wear of the surface goes deep enough into the component where the re-emission portion is worn away or otherwise significantly damaged, then the return signal is not provided from the re-emission portion, which indicates that the wear of the component has reached a certain depth. However, this type of wear detection sensor has limitations. For example, it is typically necessary to provide the re-emission portion at the end of the fiber.

The detection of wear on various components in the types of machines discussed above extends to the detection of actual cracks that may form in those components that occur as a result of machine use. Crack detection gages are known in the art that include equally spaced parallel strips of a conducting material that terminate to a common conductor at each end. The strips are typically attached to the component being detected by mechanical bonding, such as by cements or epoxies. Each of the individual parallel conductive strips is known to fail at approximately 2% strain. By monitoring the change in electrical resistance as a result of a failing strip, the number of broken conductive strips can be deduced, and the length of the crack can be indirectly determined.

This method includes a number of drawbacks including that the crack gage indirectly measures crack growth, element fabrication variations increase with measurement uncertainty, and the gages are limited in size due to the nature of the element, where the resistance goes up with length. Also, because the gage is electrical based it is susceptible to noise from electromagnetic fields common in certain machinery, and the gage requires a pre-determined location to be known.

It is well known that a fiber propagation core diameter of 10 μm provides multi-mode propagation. Because a 10 μm diameter cable is susceptible to breakage due to strain, it has been proposed that it be installed in a parallel grid pattern that runs perpendicular to the expected crack formation direction. It has previously been proposed to provide an array of these optical fibers on or in a substrate that is to be monitored for crack growth.

U.S. patent application Ser. No. 12/945,957, titled, Sensor Apparatus for Detecting and Monitoring a Crack Propagating Through a Structure, filed Nov. 15, 2010, assigned to the assignee of this application, discloses a crack detection system of this type. The '957 application discloses a sensor apparatus for detecting and monitoring cracks that includes a plurality of parallel optical fibers mounted to a structure being detected. A distal end of each optical fiber is coated with a fluorescent material and a light beam propagating down each optical fiber causes the fluorescent material to fluoresce, which generates a return signal. If one or more of the optical fibers is severed as a result of formation of a crack, that fiber will not provide a return signal, which provides an indication that a crack has formed, where the number of severed fibers provides an indication of the length of the crack.

SUMMARY OF THE INVENTION

In accordance with the teachings of the present invention, an optical fiber crack detector is disclosed that includes a plurality of FBG sensors positioned within one or more fibers that are operable to reflect a defined wavelength of an optical input beam. The crack detector includes a light source for generating the optical input beam that propagates down the optical fiber and interacts with the FBG sensors. A wavelength of the optical beam that is reflected by the FBG sensors is detected, and if a crack in the component damages the fiber between an FBG sensor and the detector circuit, where one or more of the reflected signals are not received, the detector knows that a crack has occurred. By strategically placing a plurality of the FBG sensors along the fiber, a crack that damages the fiber in multiple locations between multiple FBG sensors, or in multiple fibers, can provide an indication of the length of the crack.

Additional features of the present invention will become apparent from the following description and appended claims, taken in conjunction with the accompanying drawings.

BRIEF DESCRIPTION OF THE DRAWINGS

FIG. 9 is a plan view of a plurality of wear detectors attached to a component including a plurality of fibers each having a plurality of FBG sensors;

FIG. 10 is a plan view of a wear detector attached to a component and including a single optical fiber having a plurality of FBG sensors;

DETAILED DESCRIPTION OF THE EMBODIMENTS

The following discussion of the embodiments of the invention directed to a crack detector including a plurality of FBG sensors for detecting cracks and the length of cracks in a component is merely exemplary in nature, and is in no way intended to limit the invention or its applications or uses.

As will be discussed in detail below, the present invention proposes an optical fiber wear and/or crack detector that employs an optical fiber including a fiber core having a periodic pattern of core sections with a different index of refraction than the rest of the fiber core so as to define a fiber Bragg grating (FBG). As is well understood by those skilled in the art, an FBG formed in the core of an optical fiber operates as a reflector or filter where an optical signal of a certain wavelength of light is reflected by the FBG and all other wavelengths are transmitted through the FBG. The wear and/or crack detector uses the FBG as a sensor where the reflected wavelength is detected, and in the manner discussed above for the optical fiber wear and/or crack detection, damage to the FBG sensor can be identified when the reflection is lost. FBG sensors have heretofore been known in the art for measuring temperature or strain, but not to indicate the depth of wear or the length of a crack on a component.

Figure 1:
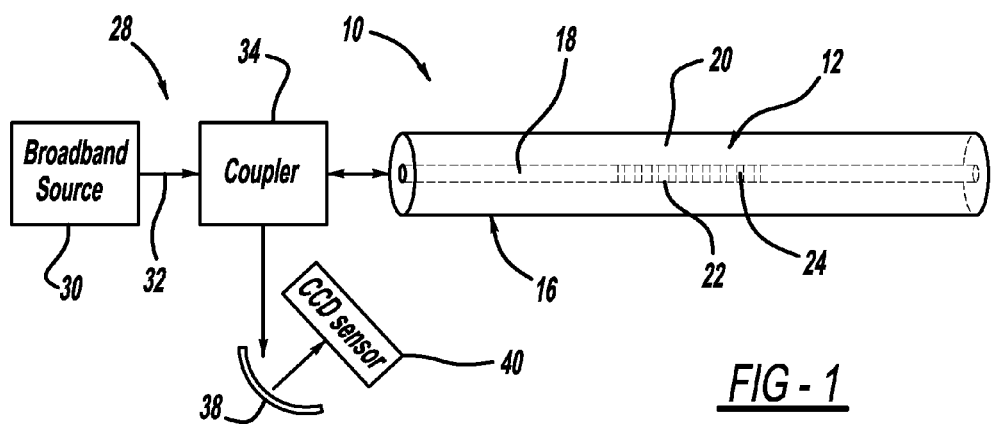
FIG. 1 is a schematic plan view of a wear detector system including an FBG sensor and detector circuitry.
Figure 2:
FIG. 2 is a graph with position on the horizontal axis and index of refraction on the vertical axis showing the index of refraction of an FBG sensor.

FIG. 1 is a schematic plan view of a wear and/or crack detection system 10 including an FBG sensor 12 formed in part of an optical fiber 16. The optical fiber 16 includes an optical fiber core 18 surrounded by an outer cladding layer 20. The index of refraction of the cladding layer 20 is greater than the index of refraction of the fiber core 18 so that a light beam propagating down the fiber core 18 is reflected off of the transition between the fiber core 18 and the cladding layer 20 and is trapped therein. In one embodiment, the fiber core 18 is about 10 μm in diameter, which provides a multi-mode fiber for propagating multiple optical modes. The FBG sensor 12 is provided in the optical fiber 16 by creating an FBG 22 using a suitable optical writing process to provide a periodic pattern of sections 24 in the fiber core 18, where the sections 24 have a higher index of refraction than the rest of the fiber core 18, but a lower index of refraction than the cladding layer 20. For example, as shown partly by the graph in FIG. 2, the index of refraction $n_3$ of the sections 24 is greater than the index of refraction $n_2$ of the fiber core 18 and the index of refraction $n_3$ of the sections 24 is less than the index of refraction $n_1$ of the cladding layer 20.

Figure 3:
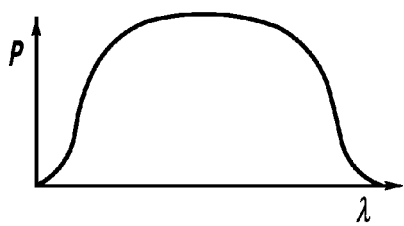
FIG. 3 is a graph with wavelength on the horizontal axis and power on the vertical axis showing the bandwidth of an input signal sent to the FBG sensor.
Figure 4:
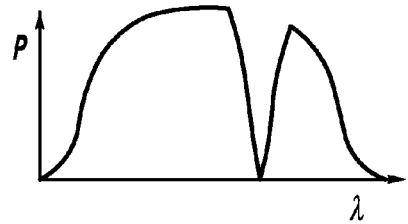
FIG. 4 is a graph with wavelength on the horizontal axis and power on the vertical axis showing the transmitted portion of the input signal through the FBG sensor.
Figure 5:
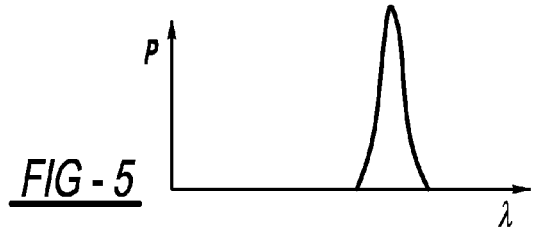
FIG. 5 is a graph with wavelength on the horizontal axis and power on the vertical axis showing the reflected portion of the input signal from the FBG sensor.

FIG. 3 is a graph with wavelength λ on the horizontal axis and power P on the vertical axis showing a wide bandwidth optical input signal that can propagate down the fiber core 18. FIG. 4 is a graph with wavelength λ on the horizontal axis and power P on the vertical axis showing the portion of the input signal that is transmitted through the FBG 22. FIG. 5 is a graph with wavelength λ on the horizontal axis and power P on the vertical axis showing the portion of the optical input signal that is reflected by the FBG 22, and having a peak at wavelength $\lambda_B$.

As is known by those skilled in the art, the FBG 22 can be selectively designed so that the index of refraction $n_2$ of the fiber core 18, the index of refraction $n_3$ of the sections 24, and the spacing Λ between the sections 24 define which wavelength $\lambda_B$ is reflected by the FBG 22 based on equation (1) below.

$$\lambda_B = 2n_3\Lambda \tag{1}$$

The system 10 also includes a circuit 28 that generates the optical input signal and detects the reflected signal from the FBG 22. The circuit 28 includes a broadband light source 30 that generates a light beam 32 that is passed through an optical coupler 34 and is directed into and propagates down the optical fiber 16 towards the FBG sensor 12. The light that is reflected by the FBG sensor 12 propagates back through the optical fiber 16 and is directed by the optical coupler 34 to a dispersive element 38 that distributes the various wavelengths components of the reflected beam to different locations on a linear charge-coupled sensor (CCD) 40.

In one embodiment, the circuit 28, or an equivalent circuit, is part of an optical sensor interrogator, such as the commercially available National Instruments NI PXIe-4844. This optical sensor interrogator employs a swept frequency light source and provides four separate optical input channels that can be simultaneously sampled at 10 Hz with an 80 nm spectrum range of 1510-1590 nm that is the bandwidth of the optical input signal. Thus, each input channel in the interrogator can be coupled to a separate optical fiber including one or more FBG sensors, as discussed below. Optical switching or multiple interrogators can be used to increase the number of fibers being monitored. Because most FBG sensors occupy only a 1-5 nm range, numerous FBG sensors can be connected to each optical channel in the interrogator. For example, for an optical input beam spectrum of 1510-1590 nm, each separate channel in the interrogator can include up to fifteen FBG sensors.

Figure 6:
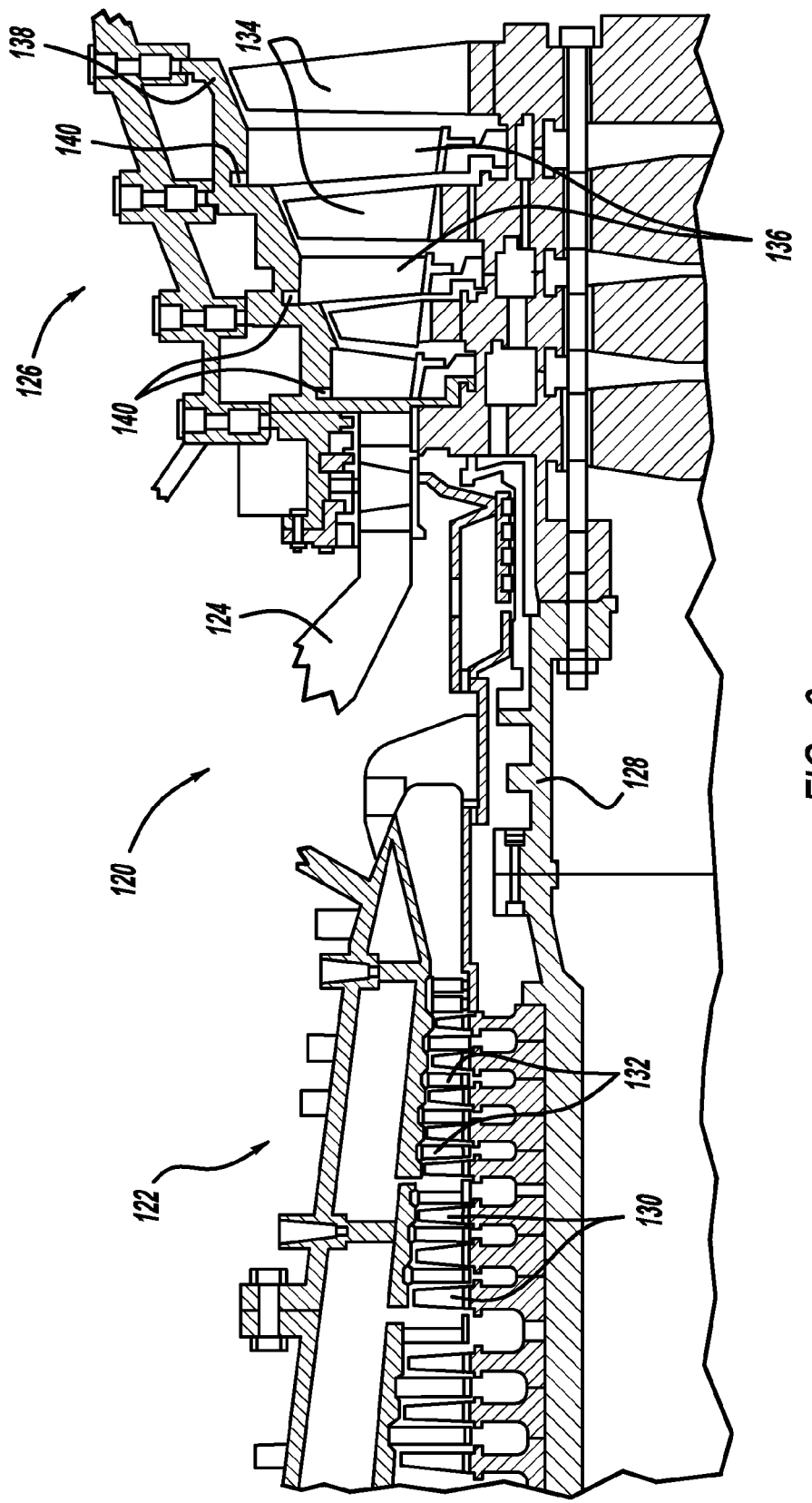
FIG. 6 is a cut-away, cross-sectional view of a gas turbine engine including one or more wear detectors including an FBG sensor.

FIG. 6 is a cut-away, cross-sectional view of a portion of a gas turbine engine 120 including a compressor section 122, a combustion section 124 and a turbine section 126, where operation of the engine 120 rotates a shaft 128. As is well understood by those skilled in the art, gas turbine engines of this type have various applications, such as electric generators in a power generating plant, aircraft engines, ship engines, etc. The compressor section 122 includes a plurality of rotatable blades 130 positioned between respective stationary vanes 132. Likewise, the turbine section 126 includes a plurality of rotatable blades 134 and stationary vanes 136 positioned therebetween. The vanes 136 are mounted to an appropriate structure within the turbine section 126 by a suitable support component 138, for example, a blade ring, as would be well understood by those skilled in the art. The blades 134 and the vanes 136 are designed for high temperature applications, and typically are made from a suitable super-alloy material, for example, a nickel, cobalt or iron based super-alloy material, which may be coated with a thermal barrier coating (TBC), for example, yttria-stabilized zirconia. The combustion section 124 includes a plurality of combustors circumferentially positioned around the turbine engine 120.

Air is drawn into the compressor section 122 where it is compressed and driven towards the combustion section 124. The combustion section 124 mixes the air with a fuel where it is ignited to generate a working gas typically having a temperature above 1300° C. The working gas expands through the turbine section 126 and is guided across the blades 134 by the vanes 136. As the working gas passes through the turbine section 126, it causes the blades 134 to rotate, which in turn causes the shaft 128 to rotate, thereby providing mechanical work. A more detailed discussion of a gas turbine engine of this type can be found in U.S. Pat. No. 7,582,359, titled Apparatus and Method of Monitoring Operating Parameters of a Gas Turbine, assigned to the assignee of this application and herein incorporate by reference.

Because of the harsh environment within the gas turbine engine 120, many of the components in the engine 120, such as the blades 130, 134 and the vanes 132, 136, may be subjected to undesirable wear. For example, during certain operating conditions, such as mechanical vibration, thermal expansion and cycling, etc., the vanes 136 and the support component 138 may have a relative movement therebetween that may cause undesirable wear on the vanes 136. Also, the turbine blades 134 may form a knife-edge seal with an abrading material at an outer edge of the blade 134, where it may be desirable to detect excessive wear or other defects in the abrading material, as is known by those skilled in the art.

As discussed herein, it may be desirable to monitor these components to detect wear and/or crack formation and provide suitable maintenance if required. For at least some of these components, one or more of the various wear and/or crack detectors employing FBG sensors discussed herein can be used to detect wear or other defects. For example, it may be desirable to provide an appropriate FBG sensor 140 positioned at the proper location in the support component 138 to detect wear and/or cracks. Other components within the engine 120 may also be applicable for a wear and/or crack detector employing an FBG sensor.

Figure 7:
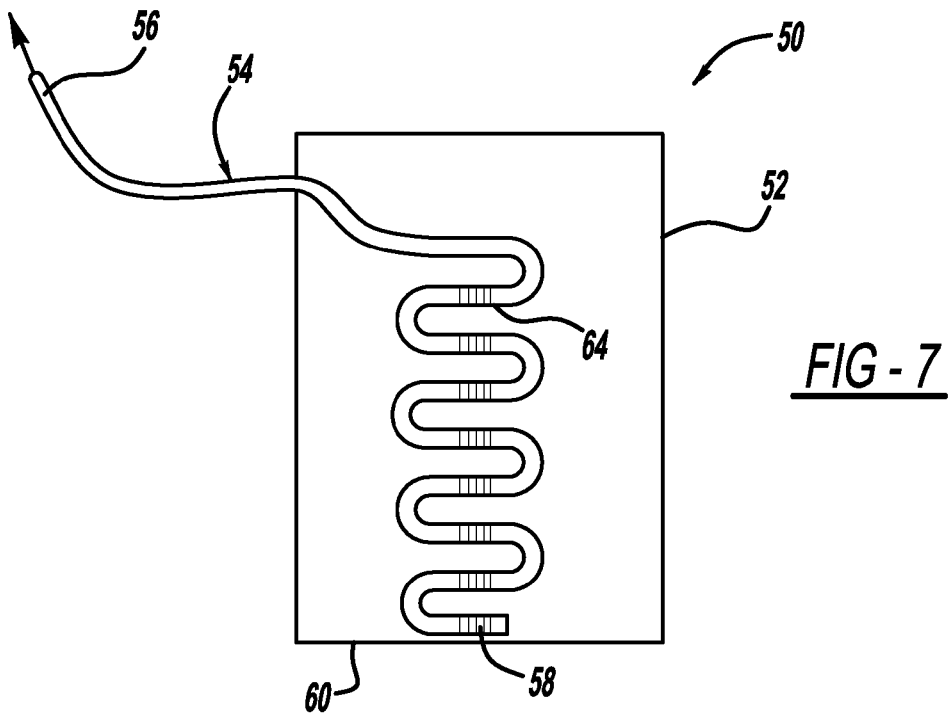
FIG. 7 is a plan view of a wear detector attached to a component and including a plurality of FBG sensors in a single fiber.

FIG. 7 is a plan view of a wear detector system 50 mounted to a component 52 that is being monitored for wear, such as cracks or other defects. The component 52 is intended to be representative of any component of any shape that the optical fiber sensors discussed herein can be mounted to. In one example, the component 52 can be part of the gas turbine engine 120. The wear detector system 50 includes a single optical fiber 54 of the type discussed above having an input end 56 that will be coupled to the appropriate circuitry, discussed above. Particularly, the end 56 of the optical fiber 54 is optically coupled to the interrogator, or other detection circuitry, from which the wide bandwidth input signal is transmitted and from which the reflected wavelength $\lambda_B$ is received.

The optical fiber 54 can be mounted to a surface of the component 52 by any technique suitable for the purposes discussed herein, such as by a suitable high temperature epoxy or ceramic cement. Alternately, the optical fiber 54 can be embedded within the component 52 by epoxying the fiber 54 into holes drilled in the component 52 or by epoxying the fiber 54 into small trenches machined in the component 52.

In this embodiment, the optical fiber 54 includes eight FBG sensors 58 spaced apart at a detection end of the optical fiber 54 opposite to the end 56 that is mounted to the component 52. The optical fiber 54 is mounted to the component 52 in such a manner that it meanders back and forth so that the FBG sensors 58 are in line with each other and spaced apart a desired distance, as shown. The FBG sensors 58 are designed so that each one reflects a different wavelength $\lambda_B$ or color consistent with equation (1). Those skilled in the art would readily recognize how to design the FBG sensors 58, whether it is one or both of the spacing $\Lambda$ of the sections 24 and the index of refraction $n_3$ of the sections 24, to achieve the desired reflected wavelength $\lambda_B$.

The component 52 being monitored has a wear surface 60 that is the direction from which the interaction with another component (not shown) would cause wear on the component 52. As the wear on the wear surface 60 occurs, each FBG sensor 58 in the line of sensors is systematically damaged so that it will not operate and reflect the wavelength $\lambda_B$ of light that it would when it is intact. Therefore, as the wear occurs, and continues to occur, the first one of the FBG sensors 58 closest to the wear surface 60 is damaged so that the analysis system will know how deep the wear has occurred based on losing that reflected signal. Each time an FBG sensor 58 is damaged, and its reflected signal is lost, the system 50 knows how deep the wear has occurred in the component 52 until it reaches the last FBG sensor 64 in the line.

Figure 8:
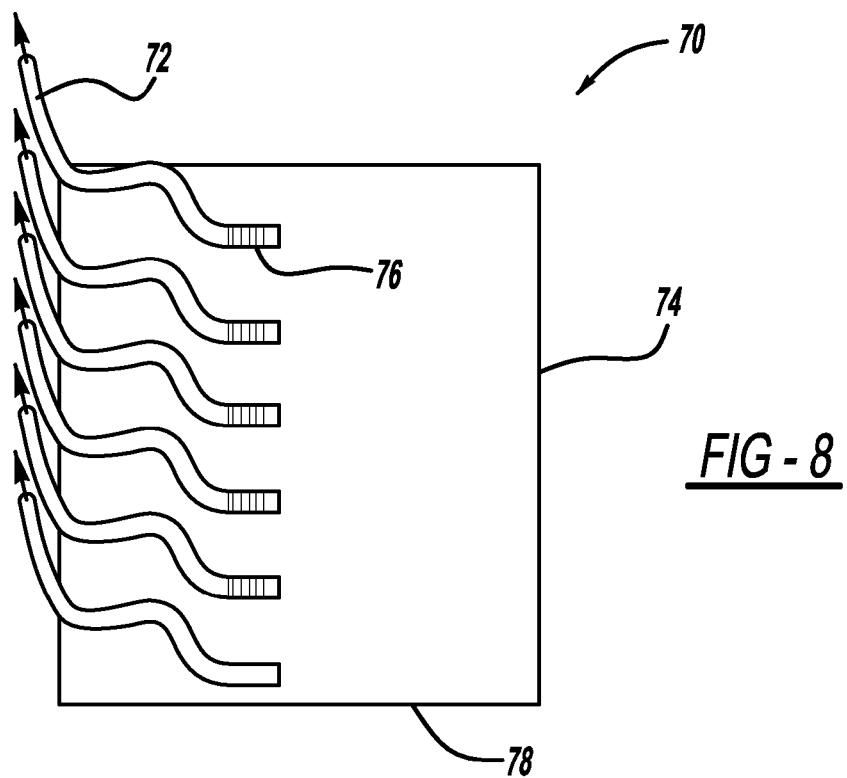
FIG. 8 is a plan view of a plurality of wear detectors attached to a component including a plurality of fibers each having a single FBG sensor.

FIG. 8 is a plan view of a wear detector system 70 including a plurality of optical fibers 72 mounted to a component 74 being monitored for wear. Each optical fiber 72 includes a single FBG sensor 76 at the end of the optical fiber 72 that is mounted to the component 74 so that all of the FBG sensors 76 are in line with each other in the same manner as the FBG sensors 58. In this embodiment, because there is a separate optical channel for each separate FBG sensor 76, the FBG sensors 76 can all reflect the same wavelength $\lambda_B$ if so desired by the user. Thus, as above, as the component 74 wears at a wear surface 78, the first FBG sensor 76 in the first optical fiber 72 is damaged and the wear detector system 70 will know the depth of the wear based on that loss of the reflected signal.

FIG. 9 is a plan view of a wear detector system 80 for detecting wear on a component 82 and including a plurality of optical fiber channels 84 each including an optical fiber 86, where each optical fiber 86 includes a plurality of spaced apart FBG sensors 88 in the optical fiber 86. In this embodiment, each optical fiber 86 includes nine FBG sensors 88, which would reflect a different wavelength $\lambda_B$ in each channel, but the corresponding FBG sensor 88 in another fiber 86 could reflect the same wavelength $\lambda_B$. Thus, a single optical fiber can detect multiple wear locations making it a multiplexed sensor. The number of FBG sensors 88 in the optical fiber 86 is limited by the bandwidth of the input optical beam. As mentioned above, for an input optical beam having a bandwidth of 1510-1590 nm, the number of FBG sensors may be limited to about fifteen.

This specialized wear detector system may be applicable for situations where there is some type of uneven wear along a wear surface 90 where different regions along the wear surface 90 are monitored for wear. For example, if there are a plurality of knife-edge seals extending along the wear surface 90 that only periodically contact the wear surface, then the wear can be separately detected at those contact locations. Thus, each line of the FBG sensors 88 would identify a particular location on the component 82 so that wear at that location can be separately identified from other locations in the component 82 corresponding to other FBG sensors 88. This embodiment will have application for circular or rounded components, as well as straight components.

FIG. 10 is a plan view of a wear detector system 100 that detects wear on a component 102 and includes a single optical fiber 104 having a plurality of FBG sensors 106 mounted to the component 102. In this design, opposite ends of the optical fiber 104 are coupled to separate channels in the analysis circuitry, which allows the system 100 alternately interrogate the fiber 104 from both ends, allowing multiple cracks to be monitored in a single fiber. In other words, separate input light beams can be sent down opposite ends of the optical fiber 104. By alternating the optical input signals sent down the optical fiber 104 in the two directions, certain defects, such as a crack or multiple cracks, can be monitored from both directions. For example, if there is a crack at wear location 110, the signal from the channel coupled to one end 112 of the optical fiber 104 can still read the FBG sensors 106 to the left of the defect and the signal from the channel coupled to the other end 114 of the optical fiber 104 can read the FBG sensors 106 at the right of the defect, which facilitates the monitoring of multiple cracks within a single fiber.

Figure 11:
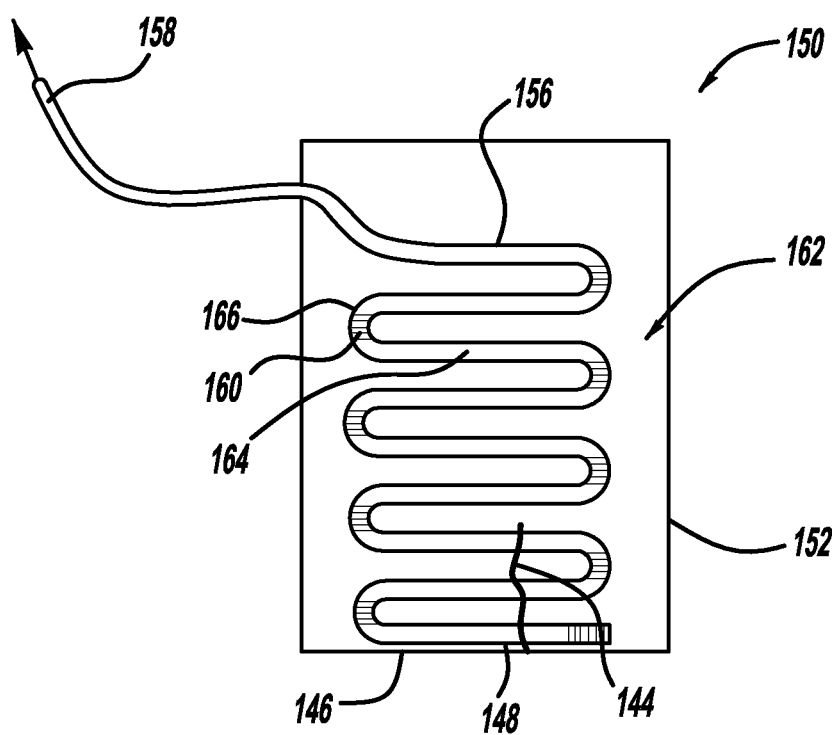
FIG. 11 is a plan view of a crack detection system mounted to a component and including a plurality of FBG sensors in a single fiber.

FIG. 11 is a plan view of a crack detection system 150 mounted to a component 152 that is being monitored for the initiation of a crack 144 and detection of the length of the crack 144, which is expected to occur, for example, along an edge 146 of the component 152 at region 148. The component 152 is intended to represent any component of any shape that the optical fiber sensors discussed herein can be mounted to. In one example, the component 52 can be part of the gas turbine engine 120, such as a turbine blade. The crack detection system 150 includes a single optical fiber 156 of the type discussed above having an input end 158 that will be optically coupled to the appropriate detection circuitry and/or devices, such as the circuit 28. Particularly, the input end 158 of the optical fiber 156 is optically coupled to the circuit 28, or other detection circuitry, that provides the wide bandwidth input signal and that detects the reflected wavelength $\lambda_B$.

The optical fiber 156 includes a detection end 162 that is mounted to a surface of the component 152 by any suitable technique for the purposes discussed herein, such as by a suitable high temperature epoxy or ceramic cement. Alternately, the optical fiber 156 can be imbedded within the component 152 by epoxying the fiber 156 into holes drilled into the component 152 or by epoxying the fiber 156 into small trenches in the machine of the component 152. The detection end 162 of optical fiber 156 is mounted to the component 152 in an orientation so that it meanders back and forth and has parallel fiber sections 164 coupled by 180° turns 166. The length of the sections 164 defines the size of the area that is being detected for cracks. FBG sensors 160 are positioned in the optical fiber 156 at the turns 166 where the fiber 156 changes direction. The turns 166 are generally semi-circular in this embodiment. However, the turns 166 can have any shape conducive for an optical fiber and where an FBG sensor of the type discussed herein can be provided.

The FBG sensors 160 are designed so that each one reflects a different wavelength $\lambda_B$ or color consistent with equation (1). Those skilled in the art would readily recognize how to design the FBG sensors 160, particularly whether it is one or both of the spacing of the sections 24 and the index of refractions $n_3$ of the sections 24, to achieve the desired reflected wavelength $\lambda_B$. If the crack 144 occurs and begins to propagate into the component 152 it will first sever or damage the fiber 156 in the last section 164 between the last two FBG sensors 160 in the fiber 156. When this incurs, the detection circuitry will not receive the wavelength $\lambda_B$ that would be reflected by the last sensor 160 in the fiber 156. As the crack progresses into the component 152, it will eventually sever or damage the fiber 156 again at the next section 164 between the second and third to last FBG sensors 160 in the fiber 156. When this occurs, the detection circuitry will not receive the reflected wavelength $\lambda_B$ from the last two FBG sensors 160 in the fiber 156. Thus, as the crack 144 continues to extend, and severs or damages the fiber 156 at the next section 164 in the meandering configuration, a loss of the reflected wavelength $\lambda_B$ from the FBG sensors 160 at the end of the fiber 156 will systematically occur, giving an indication of the length of the crack 144. The resolution of the determination of the length of the crack 144 can be controlled by determining how close the parallel sections 164 of the fiber 156 are provided to each other.

Figure 12:
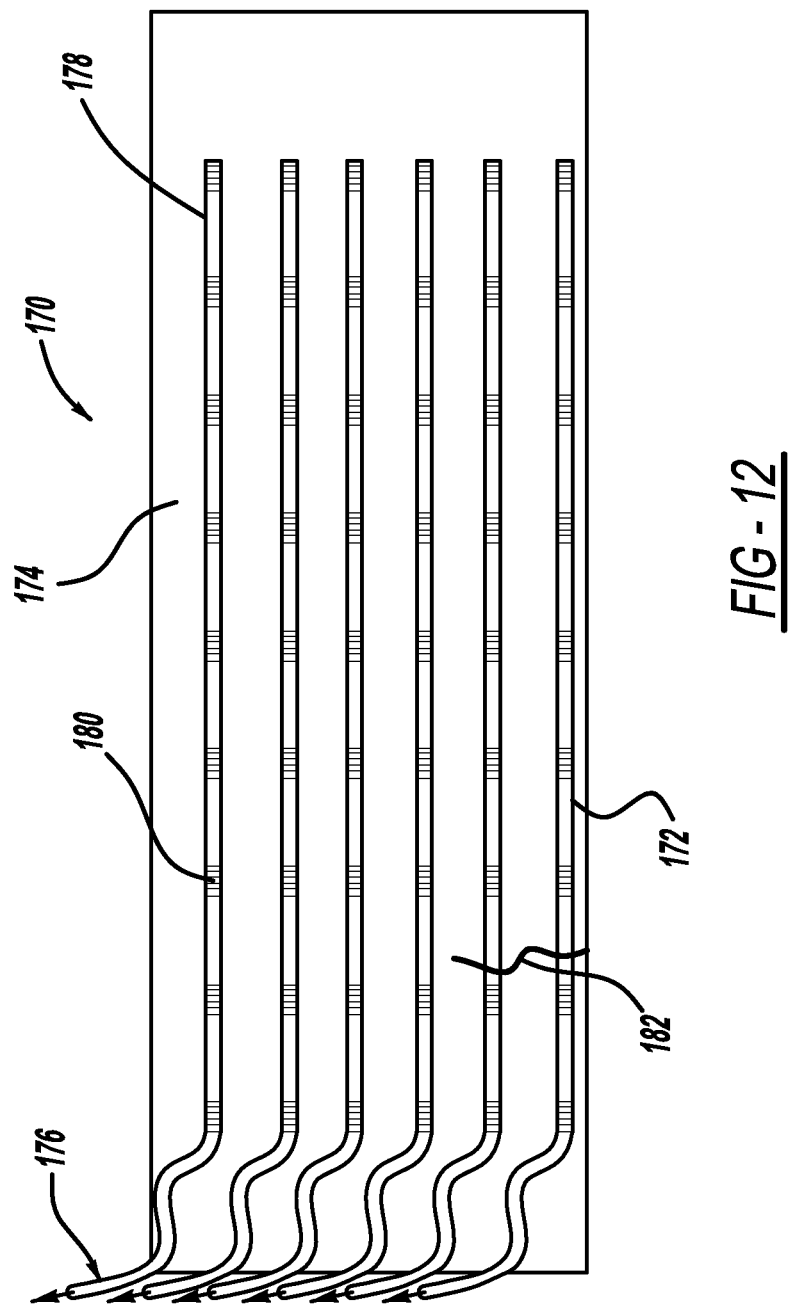
FIG. 12 is a plan view of a crack detection system including a plurality of optical fibers each including a plurality of spaced apart FBG sensors.

FIG. 12 is a plan view of a crack detection system 170 that is similar to the wear detection system 80 discussed above. The crack detection system 170 detects cracks 182 that may form at any location 172 along a defined region of a component 174. The crack detection system 170 includes a plurality of optical fiber channels 176 each including an optical fiber 178, where each optical fiber 178 includes a plurality of spaced apart FBG sensors 180. In this embodiment, each optical fiber 178 includes nine FBG sensors 180, where each sensor 180 would reflect a different wavelength $\lambda_B$ in each channel 176. The corresponding or aligned FBG sensor 180 in another fiber 178 could reflect the same wavelength $\lambda_B$. As above, if a crack initiates at the location 172 and damages the optical fiber 178 closest to the edge of the component 174, the optical fiber 178 may break or be damaged at that location. If the detection circuitry detects the reflected wavelength $\lambda_B$ from a certain number of the sensors 180 closest to the detection circuitry, but not those sensors 180 along the rest of the length of the optical fiber 178, then the system 170 will know at what location the crack 182 has occurred. The distance between the FBG sensors 180 in a particular optical fiber 178 can set the resolution of how accurately the position of the crack can be determined. As the crack 182 extends in length, it will progressively damage or sever the optical fibers 178 systematically in a direction from the edge of the component 174 so that the circuitry can monitor the length of the crack 182 as it is occurring.

The number of FBG sensors in an optical fiber and the spacing of the FBG sensors in that fiber define the length of the area that can be detected for cracks. In the crack detection system 170, nine of the FBG sensors 180 are provided. In an alternate embodiment, fifteen FBG sensors can be provided in each optical fiber 178 to detect fourteen regions for crack formation, and sixteen of the fibers 178 in separate channels could be provided for increased length detection of the crack 182.

The foregoing discussion discloses and describes merely exemplary embodiments of the present invention. One skilled in the art will readily recognize from such discussion, and from the accompanying drawings and claims, that various changes, modifications and variations can be made therein without departing from the scope of the invention as defined in the following claims.

What is claimed is:

1. A crack sensor for detecting cracks in a component, said sensor comprising:
   at least one light source generating an optical beam;
   at least one optical fiber receiving the optical beam from the at least one light source, said optical fiber including a fiber core through which the optical beam propagates and a plurality of spaced apart fiber Bragg gratings formed in the core, each fiber Bragg grating being operable to reflect a predefined and different wavelength of the optical beam back along the optical fiber and allow other wavelengths in the optical beam to propagate through the fiber Bragg grating; and
   a detector for detecting the reflected wavelengths of the optical beam from the fiber Bragg gratings, wherein a crack that forms in the component that damages or severs the fiber between fiber Bragg gratings causes loss of reflected wavelengths from at least some of the fiber Bragg gratings to identify the location of the crack.

2. The sensor according to claim 1 wherein the at least one optical fiber is mounted to the component in a meandering orientation, and wherein a separate one of the fiber Bragg gratings is positioned at each location where the optical fiber makes a 180° turn.

3. The sensor according to claim 2 wherein the meandering orientation of the optical fiber provides a plurality of substantially parallel fiber sections so that if the crack severs multiple fiber sections between the fiber Bragg gratings at the turns, the loss of the reflected wavelength from the particular fiber Bragg gratings provides an indication of the length of the crack.

4. The sensor according to claim 2 wherein the turns are semi-circular turns.

5. The sensor assembly according to claim 1 wherein the at least one optical fiber is a single optical fiber including a plurality of spaced apart fiber Bragg gratings where each fiber Bragg grating reflects a different wavelength of the optical beam, and wherein opposite ends of the optical fiber are coupled to different channels that provide different input optical beams.

6. The sensor according to claim 1 wherein the at least one optical fiber is mounted to the component in a straight line where the spaced apart fiber Bragg gratings are spaced apart along the line.

7. The sensor according claim 6 comprising a plurality of optical fibers each including a plurality of spaced apart fiber Bragg gratings, and wherein the length of the optical fibers is in a direction substantially perpendicular to a crack formation direction where damage or severing of multiple optical fibers provides an indication of the length of the crack.

8. The sensor according to claim 6 wherein each optical fiber includes fifteen fiber Bragg gratings.

9. The sensor according to claim 7 wherein each aligned fiber Bragg grating in parallel optical fibers reflects the same wavelength.

10. The sensor according to claim 1 wherein the component is part of a turbine.

11. A crack detector for detecting cracks in a component, said crack detector comprising an optical fiber including a fiber core through which an optical beam propagates and a plurality of spaced apart fiber Bragg gratings formed in the core, each fiber Bragg grating being operable to reflect a predefined and different wavelength of the optical beam back along the optical fiber and allow other wavelengths in the optical beam to propagate through the fiber Bragg grating, said optical fiber being mounted to the component in a meandering orientation defining a plurality of substantially parallel fiber sections where a separate one of the fiber Bragg gratings is positioned at each location where the optical fiber makes a 180° turn.

12. The crack detector according to claim 11 wherein the turns are semi-circular turns.

13. A crack detector for detecting cracks in a component, said crack detector comprising at least one optical fiber including a fiber core through which an optical beam propagates and a plurality of spaced apart fiber Bragg gratings formed in the core, each fiber Bragg grating being operable to reflect a predefined and different wavelength of the optical beam back along the optical fiber and allow other wavelengths in the optical beam to propagate through the fiber Bragg gratings, said optical fiber being mounted to the component in a straight line, wherein a crack that forms in the component that damages or severs the fiber between fiber Bragg gratings and causes loss of reflected wavelengths from at least some of the fiber Bragg gratings allows the detector to identify the location of the crack.

14. The crack detector according claim 13 comprising a plurality of optical fibers each including a plurality of spaced apart fiber Bragg gratings, and wherein the length of the optical fibers is in direction substantially perpendicular to a crack formation direction where damage to or severing of multiple optical fibers provides an indication of the length of the crack.

15. The crack detector according to claim 13 comprising a single optical fiber including a plurality of spaced apart fiber Bragg gratings where each fiber Bragg grating reflects a different wavelength of the optical beam, and wherein opposite ends of the optical fiber are coupled to different channels that provide different input optical beams.

16. A gas turbine comprising:
   a shaft rotatably provided along a center line of the turbine;
   a compressor section responsive to a working fluid and being operable to compress the working fluid to produce a compressed working fluid;
   a combustion section in fluid communication with the compressor section that receives the compressed working fluid, said combustion section mixing the compressed working fluid with a fuel and combusting the compressed fluid and fuel mixture to produce a hot working fluid;
   a turbine section in fluid communication with the combustion section, said turbine section expanding the hot working fluid to produce mechanical power through rotation of the shaft; and
   at least one crack sensor operatively coupled to a component in the engine, said at least one crack sensor including at least one optical fiber receiving an optical beam, said at least one optical fiber including a fiber core through which the optical beam propagates and a plurality of spaced apart fiber Bragg gratings formed in the core, each fiber Bragg grating being operable to reflect a predefined and different wavelength of the optical beam back along the optical fiber and allow other wavelengths in the optical beam to propagate through the fiber Bragg grating, wherein a crack that forms in the component that damages or severs the fiber between fiber Bragg gratings and causes loss of reflected wavelengths from at least some of the fiber Bragg gratings allows the sensor to identify the location of the crack.

17. The turbine according to claim 16 wherein the at least one optical fiber is mounted to the component in a meandering orientation, and wherein a separate one of the fiber Bragg gratings is positioned at each location where the optical fiber makes a 180° turn.

18. The turbine according to claim 17 wherein the meandering orientation of the optical fiber provides a plurality of substantially parallel fiber sections so that if the crack severs multiple fiber sections between the fiber Bragg gratings at the turns, the loss of the reflected wavelength from the particular fiber Bragg gratings provides an indication of the length of the crack.

19. The turbine according to claim 16 wherein the at least one optical fiber is mounted to the component in a straight line where the spaced apart fiber Bragg gratings are spaced apart along the line.

20. The turbine according claim 19 comprising a plurality of optical fibers each including a plurality of spaced apart fiber Bragg gratings, and wherein the length of the optical fibers is in a direction substantially perpendicular to a crack formation direction where damage or severing of multiple optical fibers provides an indication of the length of the crack.

* * * * *